(12) United States Patent
Komori et al.

(10) Patent No.: US 10,604,790 B2
(45) Date of Patent: Mar. 31, 2020

(54) SEQUENCE CONVERSION AND SIGNAL AMPLIFIER DNA CASCADE REACTIONS AND DETECTION METHODS USING SAME

(71) Applicant: ABBOTT LABORATORIES, Abbott Park, IL (US)

(72) Inventors: Makoto Komori, Matsudo (JP); Toru Yoshimura, Matsudo (JP)

(73) Assignee: ABBOTT LABORATORIES, Abbott Park, IL (US)

( * ) Notice: Subject to any disclaimer, the term of this patent is extended or adjusted under 35 U.S.C. 154(b) by 375 days.

(21) Appl. No.: 14/998,162

(22) Filed: Dec. 24, 2015

(65) Prior Publication Data

US 2016/0340710 A1 Nov. 24, 2016

Related U.S. Application Data

(60) Provisional application No. 62/096,640, filed on Dec. 24, 2014.

(51) Int. Cl.
*C12Q 1/68* (2018.01)
*C12Q 1/682* (2018.01)
*C12Q 1/6844* (2018.01)
*C12Q 1/6886* (2018.01)

(52) U.S. Cl.
CPC ............ *C12Q 1/682* (2013.01); *C12Q 1/6844* (2013.01); *C12Q 1/6886* (2013.01); *C12Q 2600/178* (2013.01)

(58) Field of Classification Search
CPC .............. C12Q 1/682; C12Q 2521/301; C12Q 2525/207
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 5,958,700 A | 9/1999 | Nadeau et al. |
| 6,316,200 B1 | 11/2001 | Nadeau et al. |
| 9,845,495 B2 | 12/2017 | Komiya |
| 2003/0082590 A1 | 5/2003 | Van Ness et al. |
| 2003/0165911 A1 | 9/2003 | Van Ness et al. |
| 2004/0259102 A1 | 12/2004 | Kool |
| 2005/0059005 A1 | 3/2005 | Tuschl et al. |
| 2008/0311564 A1 | 12/2008 | Fort |
| 2009/0017453 A1 | 1/2009 | Maples et al. |
| 2009/0081670 A1 | 3/2009 | Maples et al. |
| 2010/0129822 A1 | 5/2010 | Siva |
| 2014/0017692 A1 | 1/2014 | Komiya |
| 2015/0197823 A1 | 7/2015 | Komiya et al. |
| 2016/0102339 A1 | 4/2016 | Komiya et al. |
| 2016/0102345 A1 | 4/2016 | Komiya et al. |

FOREIGN PATENT DOCUMENTS

| | | |
|---|---|---|
| CN | 103789435 | 5/2014 |
| EP | 1500710 | 1/2005 |
| EP | 2722399 | 4/2014 |
| JP | H07114718 A | 5/1995 |
| JP | H07114718 B | 12/1995 |
| JP | 2005516610 | 6/2005 |
| WO | 200028082 | 5/2000 |
| WO | 200216639 | 2/2002 |
| WO | 2003066802 | 8/2003 |
| WO | 2004067726 | 8/2004 |
| WO | 2004067764 | 8/2004 |
| WO | 2004067765 | 8/2004 |
| WO | 2008001376 | 1/2008 |
| WO | 2009012246 | 1/2009 |
| WO | 2012077819 | 6/2012 |
| WO | 2015114469 | 8/2015 |
| WO | 2016059473 | 4/2016 |
| WO | 2016059474 | 4/2016 |

OTHER PUBLICATIONS

Tan, E. et al., "Isothermal DNA Amplification with Gold Nanosphere-Based Visual Colorimetric Readout for Herpes Simplex Virus Detection", Clinical Chemistry, 53, No. 11, pp. 2017-2020 (2007).
Tan, E. et al., "Isothermal DNA Amplification Coupled with DNA Nanosphere-Based Colorimetric Detection", Analytical Chemistry, vol. 77, No. 24, pp. 7984-7992 (Dec. 15, 2005).
Tan, E. et al., "Specific versus Nonspecific Isothermal DNA Amplification through Thermophilic Polymerase and Nicking Enzyme Activities", Biochemistry, vol. 47, No. 38, pp. 9987-9999 (2008).
G.T Walker, M.C. Little, J.G. Nadeau and D.D. Shank, Proc. Natl. Acad.Sci.USA,89, 392-396 (1992).
Y Weizmann, M.K. Beissenhirtz, Z. Cheglakov, R.Nowarski and I Willner, Angew. Chem.Inl.Ed.,45,7384-7388(2006).
International Preliminary Report, PCT/JP2011/078717, International Filing Date Dec. 12, 2011 (Tokyo Institute of Technology).
J. Van Ness, L.K. Ness, and D.J. Galas, Proc. Natl. Acad. Sci. USA, 100 (8):4504-4509 (Apr. 15, 2003).

(Continued)

*Primary Examiner* — David C Thomas
(74) *Attorney, Agent, or Firm* — Audrey L. Bartnicki; Christopher P. Singer; Frank G. Salinas

(57) ABSTRACT

Disclosed are methods for detecting a target nucleic acid in a sample. The methods include contacting the sample, in the presence of a polymerase and an endonuclease, with a first oligonucleotide comprising, in the 5' to 3' direction, a first signal DNA generation sequence, an endonuclease recognition site, and a sequence complementary to the 3' end of a target nucleic acid; a second oligonucleotide comprising, in the 5' to 3' direction, a second signal DNA generation sequence, an endonuclease recognition site, and a sequence that is homologous to the first signal DNA generation sequence of the first oligonucleotide; a third oligonucleotide comprising, in the 5' to 3' direction, a third signal DNA generation sequence, an endonuclease recognition site, and a sequence that is homologous to the second signal DNA generation sequence of the second oligonucleotide.

10 Claims, 7 Drawing Sheets

Specification includes a Sequence Listing.

(56) References Cited

OTHER PUBLICATIONS

Dirks, Robert M., Pierce, Niles A., PNAS, Oct. 26, 2004, vol. 101, No. 43, 15275-15278.
Huang, Jin, Wu, Yanrong, Chen, Van, Zhu, Zhi, Yang, Xiaohai, Yang, Chaoyong James, Wang, Kemin, Tan, Weihong, Angew. Chem.Inl.Ed. 2011,50,401-404.
Niu, Shuyan, Jiang, Yu, Zhang, Susheng, Chem. Commun., 2010, 46, 3089-3091 (2010).
International Search Report, PCT/JP2011/078717, International Filing Date Dec. 12, 2011 (Tokyo Institute of Technology).
International Search Report and Written Opinion of PCT Patent Application No. PCT/IB2015/000726, dated Sep. 10, 2015.
Gill, et al. "Nucleic Acid Isothermal Amplification Technologies—A Review", Nucleosides, Nucleotides and Nucleic Acids, Taylor & Francis, US, vol. 27, No. 3, Mar. 1, 2008, pp. 224-243.
Veedu et al., "Locked Nucleic Acids: Promising Nucleic Acid Analogs for Therapeutic Applications," Chemistry & Biodiversity, vol. 7, 2010, 7 pages.
Yang et al., "Synthesis and investigation of deoxyribonucleic acid/locked nucleic acid chimeric molecular beacons," Nucleic Acids Research, vol. 35, 2007, 9 pages.
Vester et al., "LNA (Locked Nucleic Acid): High-Affinity Targeting of Complementary RNA and DNA," Biochemistry, vol. 43, 2004, 12 pages.
PCT International Search Report and Written Opinion dated Mar. 29, 2016 for PCT Patent Application No. PCT/IB2015/002145.
International Bureau, "International Preliminary Report on Patentability", issued in connection with Application No. PCT/IB2015/002141, dated Apr. 18, 2017, 5 pages.
International Bureau, "International Preliminary Report on Patentability", issued in connection with Application No. PCT/IB2015/002145, dated Apr. 18, 2017, 9 pages.
International Search Report and Written Opinion of PCT Patent Application No. PCT/IB2015/002141, dated Apr. 6, 2016, 8 pages.
Stratagene Catalog, p. 39 (1988).
PCT, Notification of Transmittal of the International Search Report and the Written Opinion of the International Searching Authority, or the Declaration, in International Application No. PCT/IB2015/059986, dated Jun. 3, 2016 (16 pages).
Haiyun Liu et al., "High Specific and Ultrasensitive Isothermal Detection of MicroRNA by Paddlock Prob-Based Exponential Rolling Circle Amplification", Analytical Chemistry, vol. 85, No. 16, Aug. 20, 2013 (Aug. 20, 2013), pp. 7941-7947, XP055272748, ISSN: 0003-2700, DOI:10.1021/ac401715k abstract (7 pages).
Bin-Cheng Yin et al., "Sensitive Detection of MicroRNA in Complex Biological Samples via Enzymatic Signal Amplification Using DNA Polymerase Coupled with Nicking Endonuclease" Analytical Chemistry, vol. 85, No. 23, Dec. 3, 2013 (Dec. 3, 2013), pp. 11487-11493, XP055272740, ISSN: 0003-2700, DOI: 10.1021/ac403302a abstract (7 pages).
Lai et al., "Calibration Curves for Real-Time PCR", Clinical Chemistry 51:7, pp. 1132-1136, 2005, Molecular Diagnostics and Genetics.
Silahtaroglu et al., "Detection of microRNAs in frozen tissue sections by fluorescence in situ hybridization using locked nucleic acid probes and tyramide signal amplification", Nature Protocols, vol. 2, No. 10, Oct. 1, 2007, pp. 2520-2528.

Cascade Signal Amplifier DNA 1 (cSA DNA 1)

Converter DNA# 265

Converter DNA# 429

SEQUENCE LISTING

```
<160> NUMBER OF SEQ ID NOS: 12

<210> SEQ ID NO 1
<211> LENGTH: 55
<212> TYPE: DNA
<213> ORGANISM: Artificial Sequence
<220> FEATURE:
<223> OTHER INFORMATION: Sequence Conversion DNA (SC DNA)
<220> FEATURE:
<221> NAME/KEY: misc_feature
<222> LOCATION: (55)..(55)
<223> OTHER INFORMATION: 3'-end modification: two inverted thymidines

<400> SEQUENCE: 1
tgatagccct gtacaatgcc tcagcttgta cagggctatc actgttcctg ctgaa         55

<210> SEQ ID NO 2
<211> LENGTH: 61
<212> TYPE: DNA
<213> ORGANISM: Artificial Sequence
<220> FEATURE:
<223> OTHER INFORMATION: Cascade Sequence Amplification DNA (cSA DNA 2)
<220> FEATURE:
<221> NAME/KEY: misc_feature
<222> LOCATION: (61)..(61)
<223> OTHER INFORMATION: 3'-end modification: two inverted thymidines

<400> SEQUENCE: 2
actgccctaa gtgctcctcc tcagcaggag cacttagggc agttgatagc cctgtacaat    60
g                                                                    61

<210> SEQ ID NO 3
<211> LENGTH: 13
<212> TYPE: DNA
<213> ORGANISM: Artificial Sequence
<220> FEATURE:
<223> OTHER INFORMATION: u.particle DNA
<220> FEATURE:
<221> NAME/KEY: misc_feature
<222> LOCATION: (13)..(13)
<223> OTHER INFORMATION: 3'-u.particle

<400> SEQUENCE: 3
gtgctcctcc tca                                                       13

<210> SEQ ID NO 4
<211> LENGTH: 10
<212> TYPE: DNA
<213> ORGANISM: Artificial Sequence
<220> FEATURE:
<223> OTHER INFORMATION: Conjugate DNA
<220> FEATURE:
<221> NAME/KEY: misc_feature
<222> LOCATION: (1)..(1)
<223> OTHER INFORMATION: 5'-Acridinium

<400> SEQUENCE: 4
actgccctaa                                                           10
```

```
<210> SEQ ID NO 5
<211> LENGTH: 22
<212> TYPE: DNA
<213> ORGANISM: Artificial Sequence
<220> FEATURE:
<223> OTHER INFORMATION: Target DNA

<400> SEQUENCE: 5
tggctcagtt cagcaggaac ag                                              22

<210> SEQ ID NO 6
<211> LENGTH: 23
<212> TYPE: DNA
<213> ORGANISM: Artificial Sequence
<220> FEATURE:
<223> OTHER INFORMATION: Signal DNA

<400> SEQUENCE: 6
tgaggaggag cacttagggc agt                                             23

<210> SEQ ID NO 7
<211> LENGTH: 53
<212> TYPE: DNA
<213> ORGANISM: Artificial Sequence
<220> FEATURE:
<223> OTHER INFORMATION: Sequence Conversion DNA (SC DNA)
<220> FEATURE:
<221> NAME/KEY: misc_feature
<222> LOCATION: (53)..(53)
<223> OTHER INFORMATION: 3'-end modification: one inverted thymidine

<400> SEQUENCE: 7
gcgatgatga tcctcagcgg atcatcatcg cctgttcctg ctgaactgag cca            53

<210> SEQ ID NO 8
<211> LENGTH: 57
<212> TYPE: DNA
<213> ORGANISM: Artificial Sequence
<220> FEATURE:
<223> OTHER INFORMATION: Cascade Sequence Amplification DNA (cSA DNA 1)
<220> FEATURE:
<221> NAME/KEY: misc_feature
<222> LOCATION: (57)..(57)
<223> OTHER INFORMATION: 3'-end modification: one inverted thymidine

<400> SEQUENCE: 8
tgatagccct gtacaatgcc tcagcttgta cagggctatc agcgatgatg atcctca        57

<210> SEQ ID NO 9
<211> LENGTH: 23
<212> TYPE: DNA
<213> ORGANISM: Artificial Sequence
<220> FEATURE:
<223> OTHER INFORMATION: Signal DNA

<400> SEQUENCE: 9
tgaggtggag aagatacgca aga                                             23

<210> SEQ ID NO 10
<211> LENGTH: 23
<212> TYPE: DNA
<213> ORGANISM: Artificial Sequence
<220> FEATURE:
<223> OTHER INFORMATION: Signal DNA

<400> SEQUENCE: 10
```

```
tgaggttctg ctatgttgct gct                                              23
```

```
<210> SEQ ID NO 11
<211> LENGTH: 61
<212> TYPE: DNA
<213> ORGANISM: Artificial Sequence
<220> FEATURE:
<223> OTHER INFORMATION: Cascade Sequence Amplification DNA (cSA DNA)
<220> FEATURE:
<221> NAME/KEY: misc_feature
<222> LOCATION: (61)..(61)
<223> OTHER INFORMATION: 3'-end modification: two inverted thymidines

<400> SEQUENCE: 11
agcagcaaca tagcagaacc tcagcttctg ctatgttgct gcttcttgcg tatcttctcc a    61

<210> SEQ ID NO 12
<211> LENGTH: 61
<212> TYPE: DNA
<213> ORGANISM: Artificial Sequence
<220> FEATURE:
<223> OTHER INFORMATION: Cascade Sequence Amplification DNA (cSA DNA)
<220> FEATURE:
<221> NAME/KEY: misc_feature
<222> LOCATION: (61)..(61)
<223> OTHER INFORMATION: 3'-end modification: two inverted thymidines

<400> SEQUENCE: 12
tcttgcgtat cttctccacc tcagctggag aagatacgca agaagcagca acatagcaga a    61
```

SEQUENCE CONVERSION AND SIGNAL AMPLIFIER DNA CASCADE REACTIONS AND DETECTION METHODS USING SAME

CROSS-REFERENCE TO RELATED APPLICATIONS

This application claims the benefit of priority to U.S. Provisional Patent application Ser. No. 62/096,640, filed Dec. 24, 2014, the entirety of which is hereby incorporated by reference.

SEQUENCE LISTING

This application contains a Sequence Listing which is incorporated by reference and is submitted with the filing of this application as both a computer readable CD and paper form entitled, "12351USO1_SeqListToFile.TXT". The Sequence Listing file was created on Dec. 24, 2015 and is 3,522 bytes in size.

FUNDING

[Not Applicable]

BACKGROUND

The detection of target nucleic acid in test samples is important in various fields, including medicine and biology. Many compositions, assay platforms, and procedures are available for the detection of specific nucleic acid molecules. In order for detection to be reproducible and accurate, these procedures require selectivity and sensitivity adequate to allow for the detection of nucleic acid molecules present at low concentrations.

One common method used for amplification of specific sequences from a population of mixed nucleic acid sequences is the polymerase chain reaction (PCR). Since a typical PCR is carried out at three different temperatures, the reaction can be associated with challenges such as difficulty in maintaining accurate temperatures and that the time loss increases in proportion to the number of amplification cycles. The denaturation of a double-stranded template DNA into single strands (while dependent to some extent on the particular sequence) often requires the use of high "melting" temperatures, which limits the class of DNA polymerases that can be used to those that are highly thermostable. Consequently, isothermal amplification platform technologies have been developed to detect nucleic acids under reaction conditions that are milder than those used in PCR. Nevertheless, these isothermal amplification technologies have challenges that are presented by non-specific amplification events and high background signals, as well as challenges with selectivity and sensitivity in the detection of target nucleic acids at low concentrations.

The following disclosure provides alternative methods and compositions for detecting a nucleic acid sequence (such as DNA or RNA) under reaction conditions that are less rigorous than those used in PCR. The methods and compositions maintain sequence selectivity and sensitivity that allows for the detection of nucleic acid molecules that may be in a sample at low concentrations and/or nucleic acid molecules of a short length. Among other aspects, the disclosure provides novel methods and nucleic acid molecules that can improve the detection limit of target nucleic acids in a sample under low temperature, isothermal conditions, and can simplify or improve sample preparation and automated methods of detection.

SUMMARY OF THE INVENTION

In one aspect, the disclosure relates to methods for detecting a target nucleic acid in a sample, wherein the interaction of a target nucleic acid with a first oligonucleotide (sequence conversion DNA or SC DNA) produces a first signal DNA (S1) that in turn interacts with a second oligonucleotide (cascade signal amplifier DNA 1 or cSA DNA 1) to produce a second signal DNA (S2) different from S1, which in turn can interact with a third oligonucleotide (cascade signal amplifier DNA 2 or cSA DNA 2) to produce a third unique signal DNA (S3). The third unique signal DNA S3 can interact with a fourth oligonucleotide (cascade signal amplifier DNA 3 or cSA DNA 3) to produce a fourth unique signal DNA (S4), which in turn can interact with a fifth oligonucleotide (cascade signal amplifier DNA 4 or cSA DNA 4) to produce a fifth unique signal DNA S5, which in turn can interact with a sixth oligonucleotide (cascade signal amplifier DNA 5 or cSA DNA 5) to produce a sixth unique signal DNA S5, and so on until the desired amplification is reached.

For example, the disclosure relates to a method for detecting a target nucleic acid in a sample, said method comprising contacting said sample with: a first oligonucleotide (sequence conversion DNA or SC DNA) comprising, in the 5' to 3' direction, a first signal DNA generation sequence (A), an endonuclease recognition site (B), and a sequence (C) complementary to the 3' end of a target nucleic acid; a second oligonucleotide (cascade signal amplifier DNA 1 or cSA DNA 1) comprising, in the 5' to 3' direction, a second unique signal DNA generation sequence (D), an endonuclease recognition site (E) (which may be the same or different from the endonuclease recognition site (B) in the SC DNA), and a sequence (F) that is homologous to the first signal DNA generation sequence (A) of the first SC DNA oligonucleotide; a polymerase; and an endonuclease for a nicking reaction. As discussed above, nth unique cascade signal amplifier DNAs (or cSA DNAs) can be added to the reaction above, each unique cSA DNA generating a unique Signal DNA. For example, n can be 10, 9, 8, 7, 5, 4, 3, 2, or 1, in which case 10, 9, 8, 7, 5, 4, 3, 2, or 1 different cSA DNAs are added to a reaction comprising a target nucleic acid and sequence conversion DNA (scDNA). In embodiments of this aspect, the method also comprises determining the presence or absence of one or more signal DNA(s), wherein the presence of the one or more signal DNA(s) indicates the presence of the target nucleic acid in the sample.

For example, the disclosure also relates to a method for detecting a target nucleic acid in a sample, said method comprising contacting said sample with: a first oligonucleotide (sequence conversion DNA or SC DNA) comprising, in the 5' to 3' direction, a first signal DNA generation sequence (A), an endonuclease recognition site (B), and a sequence (C) complementary to the 3' end of a target nucleic acid; a second oligonucleotide (cascade signal amplifier DNA 1 or cSA DNA 1) comprising, in the 5' to 3' direction, a second unique signal DNA generation sequence (D), an endonuclease recognition site (E) (which may be the same or different from the endonuclease recognition site (B) in the SC DNA), and a sequence (F) that is homologous to the first signal DNA generation sequence (A) of the first SC DNA oligonucleotide; a third oligonucleotide (cascade signal amplifier DNA 2 or cSA DNA 2) comprising, in the 5' to 3' direction, a third unique signal DNA generation sequence (G), an endonuclease recognition site (H) (which may be the same or different from the endonuclease recognition sites (B) and (E)), and a sequence (I) that is homologous to the second signal DNA generation sequence (D) of the second oligonucleotide cSA DNA 1; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In another aspect, the disclosure relates to methods for detecting a target nucleic acid in a sample, wherein the interaction of a target nucleic acid with a first oligonucleotide (sequence conversion DNA or SC DNA) produces a first signal DNA (S1) that in turn interacts with a second oligonucleotide (cascade signal amplifier DNA 1 or cSA DNA 1) to produce a second signal DNA (S2) different from S1, which in turn can interact with a third oligonucleotide (cascade signal amplifier DNA 2 or cSA DNA 2) to produce Signal DNA (S1), which is the same Signal DNA generated upon interaction of the target nucleic acid with SC DNA. In this aspect, amplified Signal DNA (S2) is converted to Signal DNA (S1) upon interaction with cascade signal amplifier DNA cSA DNA 2, allowing cyclic amplification of signal DNA (S1).

The SC and/or cSA DNAs of the present disclosure are generally linear, however these DNAs can also be circular (i.e. mini-circle DNA (mc)). Rolling circle amplification (RCA) can be primed upon binding of the 3' end of a target nucleic acid to a mini-circle SC DNA, or upon binding of the 3' end of a signal DNA to a mini-circle cSA DNA. The resulting RCA product is a long single-stranded DNA fragment containing thousands of copies of the SC DNA or cSA DNA.

In one example, the signal DNA generation sequence (A) of a SC DNA can be complementary to the 5'-end of a target nucleic acid (T). In this aspect, the target nucleic acid (T) binds to both the signal DNA generation sequence (A) and the sequence (C) of the SC DNA. The binding of target nucleic acid (T) to the SC DNA (in the presence of DNA ligase) results in the formation of a mini-circle SC DNA (mc SC DNA), and subsequent priming of rolling circle amplification (RCA). The resulting RCA product is a long single-stranded DNA fragment containing thousands of copies of the SC DNA. In one embodiment the endonuclease recognition site of the SC DNA is within the double-stranded stem-loop region of a hairpin structure, and therefore subject to nicking (on the 3' side of the stem-loop) in the presence of a nicking endonuclease. In the presence of both a nicking endonuclease and polymerase, signal DNA can be generated directly from the RCA product.

The methods and oligonucleotides of the present disclosure can be used in combination with other amplification and/or detection schemes. For example, any one of the signal DNAs produced in accordance with the methods disclosed herein can serve as a primer in a rolling circle amplification reaction. In one embodiment, the 3' end of a signal DNA produced according to methods of the present disclosure can be complementary to a mini-circle DNA template, and rolling circle amplification can be initiated upon binding of the signal DNA.

The disclosure also provides for nucleic acid molecules (e.g., SC and cSA DNAs as disclosed herein), compositions, kits, and methods that allow for measurement of signal DNAs that indicate the presence of a target nucleic acid. For example, in some embodiments a signal resulting from the presence of from about 1 nM to about 1 fM target nucleic acid in a sample is detectable within about 10 to about 120, about 5 to about 120, or about 3 to about 120 minutes.

In embodiments of this aspect the polymerase may have strand displacement activity. In further embodiments, the polymerase may be 3' to 5' exonuclease deficient, 5' to 3' exonuclease deficient, or both 3' to 5' exonuclease deficient and 5' to 3' exonuclease deficient. In some embodiments the polymerase comprises a DNA polymerase.

In embodiments, the endonuclease may comprise a nicking endonuclease or a restriction endonuclease that can be used in a reaction that nicks an oligonucleotide. Endonuclease recognition sites (B) of the SC DNA, (E) of the first cSA DNA 1, and H of the second cSA DNA 2 can be identical, different, or a combination wherein two are identical and the third is different.

While the method disclosed herein may be performed under typical DNA amplification conditions (e.g., typical temperatures associated with standard PCR, reactant concentrations, time cycles, etc.), in some embodiments the method may be performed under isothermal conditions or under substantially constant temperatures. In further embodiments the method may be performed at temperatures that are lower than temperatures used in standard PCR methods. As one example, some embodiments of the method may be performed at a temperature at or below a calculated optimal hybridization or annealing temperature, or an experimentally determined hybridization or annealing temperature, of the target nucleic acid (T) and the sequence (C) of the SC DNA, or of a signal DNA and the complementary sequence of a cSA DNA as described below. In embodiments, the method may be performed at a temperature that is below the melting temperature of the target nucleic acid (T) bound to the sequence (C) of the SC DNA, or a signal DNA bound to the sequence of a cSA DNA. In yet other embodiments, the method may be performed at temperatures that allow for polymerase and/or endonuclease activity. In further embodiments, the method may be performed at temperatures that are at or about the optimal reaction temperature for the polymerase and/or endonuclease present in the reaction mixture for the detection of a target nucleic acid in a sample.

In another aspect, the disclosure relates to an oligonucleotide, which may be referred herein as a "sequence conversion DNA" (or "SC DNA") comprising, in the 5' to 3' direction, a first signal DNA generation sequence (A), an endonuclease recognition site (B), and a sequence (C) complementary to the 3' end of a target nucleic acid.

In another aspect, the disclosure relates another oligonucleotide, which may be referred to herein as a "first cascade signal amplifier DNA 1" (or "cSA DNA 1") comprising, in the 5' to 3' direction, a second unique signal DNA generation sequence (D), an endonuclease recognition site (E), and a sequence which is homologous to a signal DNA generation sequence (A) of a sequence conversion DNA (SC DNA).

In another aspect, the disclosure relates another oligonucleotide, which may be referred to herein as a "second cascade signal amplifier DNA 2" (or "cSA DNA 2") comprising, in the 5' to 3' direction, a third unique signal DNA generation sequence (G), an endonuclease recognition site (H), and a sequence which is homologous to a signal DNA generation sequence (D) of a first cascade signal amplifier DNA 1 (cSA DNA 1).

The target nucleic acid sequence may be any nucleotide sequence of interest and in some embodiments may comprise a sequence that originates from an infectious agent or a microRNA. In other embodiments the target nucleic acid may comprise a sequence from a gene that may be associated with a disease or a disorder.

In some embodiments the endonuclease recognition sites (B), (E), and (H) comprises a sequence that is complementary to a sequence that is nicked by an endonuclease. In other embodiments, the sequence that is nicked by the endonuclease is adjacent (downstream or upstream) to the sequence that is specifically recognized by the endonuclease.

In a further aspect, the disclosure relates to a composition for detecting a target nucleic acid in a sample, said composition comprising: a first oligonucleotide (sequence conversion DNA or SC DNA) comprising, in the 5' to 3' direction, a first unique signal DNA generation sequence (A), an endonuclease recognition site (B), and a sequence (C) complementary to the 3' end of a target nucleic acid; a second oligonucleotide (cascade signal amplifier DNA 1 or cSA DNA 1) comprising, in the 5' to 3' direction, a second unique signal DNA generation sequence (D), an endonuclease recognition site (E), and a sequence (F) that is homologous to the first signal DNA generation sequence (A) of the first SC DNA oligonucleotide; a third oligonucleotide (cascade signal amplifier DNA 2 or cSA DNA 2) comprising, in the 5' to 3' direction, a third unique signal DNA generation sequence (G), an endonuclease recognition site (H), and a sequence (I) that is homologous to the second signal DNA generation sequence (D) of the second oligonucleotide cSA DNA 1; a polymerase; and an endonuclease for a nicking reaction. In embodiments of this aspect, the compositions are used in methods for determining the presence or absence of a signal DNA, wherein the presence of the signal DNA indicates the presence of the target nucleic acid in the sample.

The compositions can also comprise a polymerase, and/or an endonuclease capable of nicking at or adjacent to the endonuclease recognition sites (endonuclease recognition site (B) of the SC DNA, endonuclease recognition site (E) of the first cSA DNA 1, and endonuclease recognition site (H) of the second cSA DNA 2), when the endonuclease recognition sites are double stranded. Compositions can also include other reagents such as reaction buffers, deoxyribonucleotides, and reporter molecules such as, for example, fluorophore-modified probe DNAs (e.g., molecular beacon probes) for the fluorescent detection of newly synthesized DNA.

In yet another aspect, the disclosure relates to a kit for detecting a target nucleic acid in a sample, said kit comprising: a first oligonucleotide (sequence conversion DNA or SC DNA) comprising, in the 5' to 3' direction, a first signal DNA generation sequence (A), an endonuclease recognition site (B), and a sequence (C) complementary to the 3' end of a target nucleic acid; a second oligonucleotide (cascade signal amplifier DNA 1 or cSA DNA 1) comprising, in the 5' to 3' direction, a second unique signal DNA generation sequence (D), an endonuclease recognition site (E), and a sequence (F) that is homologous to the first signal DNA generation sequence (A) of the first SC DNA oligonucleotide; and a third oligonucleotide (cascade signal amplifier DNA 2 or cSA DNA 2) comprising, in the 5' to 3' direction, a third unique signal DNA generation sequence (G), an endonuclease recognition site (H), and a sequence (I) that is homologous to the second signal DNA generation sequence (D) of the second oligonucleotide cSA DNA 1. In some embodiments the kits can further comprise a polymerase and/or an endonuclease capable of nicking an endonuclease recognition site or a site adjacent to an endonuclease recognition site. The kits can also include reagents such as reaction buffers, deoxyribonucleotides, and reporter molecules such as, for example, fluorophore-modified probe DNAs (e.g., molecular beacon probes) for the fluorescent detection of newly synthesized DNA such as a signal DNA. The kits can also comprise instructions for use in the practice of any one of the methods disclosed herein.

The methods, oligonucleotides, compositions, and kits disclosed herein may be used in combination with integrated system platforms. For example, methods, oligonucleotides, compositions, and kits of the present invention may be used in combination Abbott's ARCHITECT system. The methods, oligonucleotides, compositions, and kits disclosed herein may be used with sample preparation system platforms such as, for example, the m2000sp sample preparation system (Abbott Diagnostics, Abbott Park, Ill.). Similarly, the methods, oligonucleotides, compositions, and kits disclosed herein may be used with point-of-care system platforms such as, for example, Abbott's i-STAT point-of-care system (Abbott Diagnostics, Abbott Park, Ill.). Further, the methods, oligonucleotides, compositions, and kits of the present invention can be used with any number of other devices, assay platforms, and instrumentation such as, for example, hand held fluorescence detectors, micro-pH meters, microfluidic devices, microarrays, enzymatic detection systems, immunochromatographic strips, and lateral flow devices.

The methods, oligonucleotides, compositions, and kits disclosed herein may be used in the field of molecular diagnostics, including diagnosis of non-infectious and infectious diseases. For example, methods, oligonucleotides, compositions, and kits of the present invention can be used to detect cancers and other genetic diseases. Similarly, methods, oligonucleotides, compositions, and kits of the present invention can be used to detect target nucleic acids originating from infectious diseases such as, for example, hepatitis B virus, hepatitis C virus, human immunodeficiency virus, *Chlamydia trachomatis, Neisseria gonorrhoeae*, influenza A virus, influenza B virus, or respiratory syncytial virus.

Additional aspects, embodiments, and advantages provided by the disclosure will become apparent in view of the description that follows.

DETAILED DESCRIPTION

In a general sense, the disclosure relates to nucleic acid constructs that are surprisingly effective in the detection of target nucleic acids in a test sample. The constructs disclosed herein comprise nucleic acid sequences that allow the production of signal DNAs that are generated in the presence of a target nucleic acid. The methods and nucleic acid constructs disclosed herein provide for selective and sensitive detection of target nucleic acids that may be advantageously performed under low temperature and isothermal conditions.

In embodiments of this aspect, the disclosure provides novel Sequence Conversion (SC) and cascade Signal Amplifier (cSA) oligonucleotide constructs, and combinations thereof, that are useful in detecting a target nucleic acid in a sample. As depicted by the illustrative embodiment of FIG. 1A, a Sequence Conversion DNA (SC DNA) oligonucleotide for the detection of a target nucleic acid in a sample comprises, in the 5' to 3' direction, a first signal generation sequence (A), an endonuclease recognition site (B) that can be used in a nicking reaction, and a sequence (C) complementary to the target nucleic acid As depicted by the illustrative embodiment of FIG. 1B, a first cascade Signal Amplifier DNA (cSA DNA 1) for the detection of a target nucleic acid in a sample comprises, in the 5' to 3' direction, a second unique signal DNA generation sequence (D); an endonuclease recognition site (E), and a sequence (F) that is homologous to the first signal DNA generation sequence (A) of a first SC DNA.

Figure 1A:
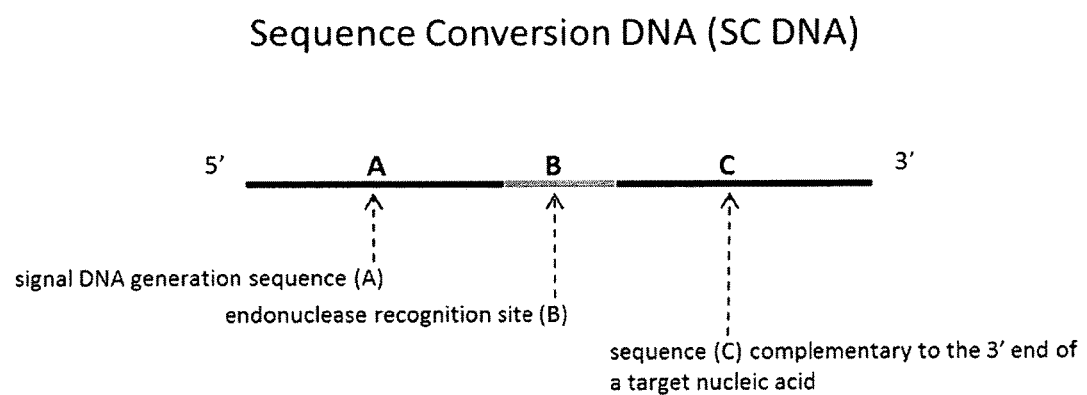
FIG. 1A is a diagram schematically illustrating a non-limiting example of a Sequence Conversion DNA (SC DNA) for the detection of a target nucleic acid in a sample. The SC DNA comprises, in the 5' to 3' direction, a first signal generation sequence (A), an endonuclease recognition site (B) that can be used in a nicking reaction, and a sequence (C) complementary to the target nucleic acid.
Figure 1B:
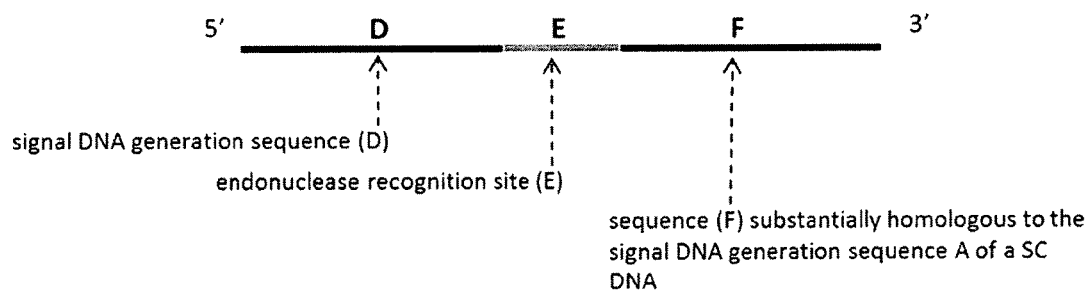
FIG. 1B is a diagram schematically illustrating a non-limiting example of a first cascade Signal Amplifier DNA 1 (cSA DNA 1) for the detection of a target nucleic acid in a sample. The cSA DNA 1 comprises, in the 5' to 3' direction, a second unique signal DNA generation sequence (D); an endonuclease recognition site (E), and a sequence (F) that is homologous to the first signal DNA generation sequence (A) of a first SC DNA.
Figure 1C:
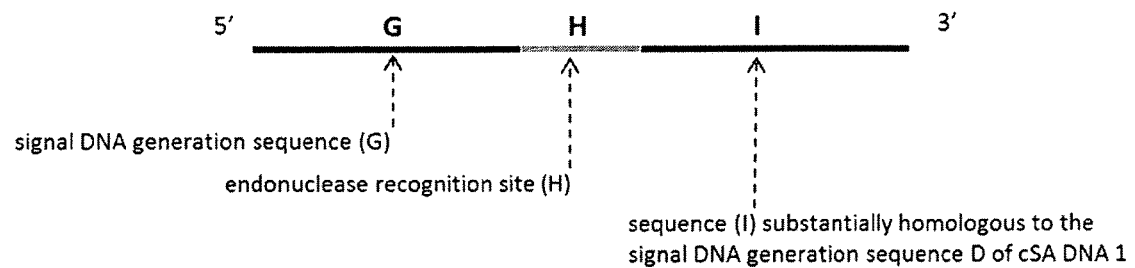
FIG. 1C is a diagram schematically illustrating a non-limiting example of a second cascade Signal Amplifier DNA 2 (cSA DNA 2) for the detection of a target nucleic acid in a sample. The cSA DNA 2 comprises, in the 5' to 3' direction, a third signal DNA generation sequence (G); an endonuclease recognition site (H), and a sequence (I) that is homologous to the second signal DNA generation sequence (D) of a first cSA DNA 1.

As depicted by the illustrative embodiment of FIG. 1C, a second cascade Signal Amplifier DNA 2 (cSA DNA 2) for the detection of a target nucleic acid in a sample comprises, in the 5' to 3' direction, a third unique signal DNA generation sequence (G); an endonuclease recognition site (H), and a sequence (I) that is homologous to the second signal DNA generation sequence (D) of a first cSA DNA 1.

As illustrated in FIG. 1A, the SC DNAs disclosed herein comprise a first signal generation sequence (A). The signal generation sequence (A) in the SC DNA can comprise any desired nucleic acid sequence and is not limited by any particular sequence. As discussed in greater detail below, the signal generation sequence (A) provides at least a portion of the template for a first signal DNA (S1). The signal generation sequence (A) in the SC DNA is not limited by length. In some embodiments, the signal generation sequence (A) in the SC DNA is from about 5 to about 100 nucleic acid bases, and all integers between 5 and 100. In embodiments, the signal generation sequence (A) in the SC DNA is from about 5 to about 30 nucleic acid bases, and all integers between 5 and 30. In some embodiments, the signal generation sequence (A) in the SC DNA is from about 10 to about 30 nucleic acid bases, and all integers between 10 and 30. In yet further embodiments, the signal generation sequence (A) in the SC DNA is from about 15 to about 30 nucleic acid bases, and all integers between 15 and 30 (e.g., about 16, about 17, about 18, about 19, about 20, about 21, about 22, about 23, about 24, about 25, about 26, about 27, about 28, about 29 or about 30 bases).

The SC DNA and cSA DNAs 1 and 2 comprise endonuclease recognition sites (B), (E), and (H) respectively, which can be the same or different. In single stranded form (e.g., the structure of FIGS. 1A, 1B, and 1C) the endonuclease recognition sites (B), (E), and (H) may comprise a sequence that is complementary to a sequence that may be nicked by an endonuclease. The sequence that is nicked by the endonuclease may be within, downstream, or upstream from the sequence that is recognized by the endonuclease. Suitably, when double stranded, the endonuclease recognition sites (B), (E), and (H) can be recognized by one or more endonucleases present in the reaction, and the endonuclease recognition sites (B), (E), and (H) (or a sequence adjacent to the endonuclease recognition sites (B), (E), and (H)) may be cleaved on only one strand of the double-stranded DNA (i.e., nicked).

Figure 2A:
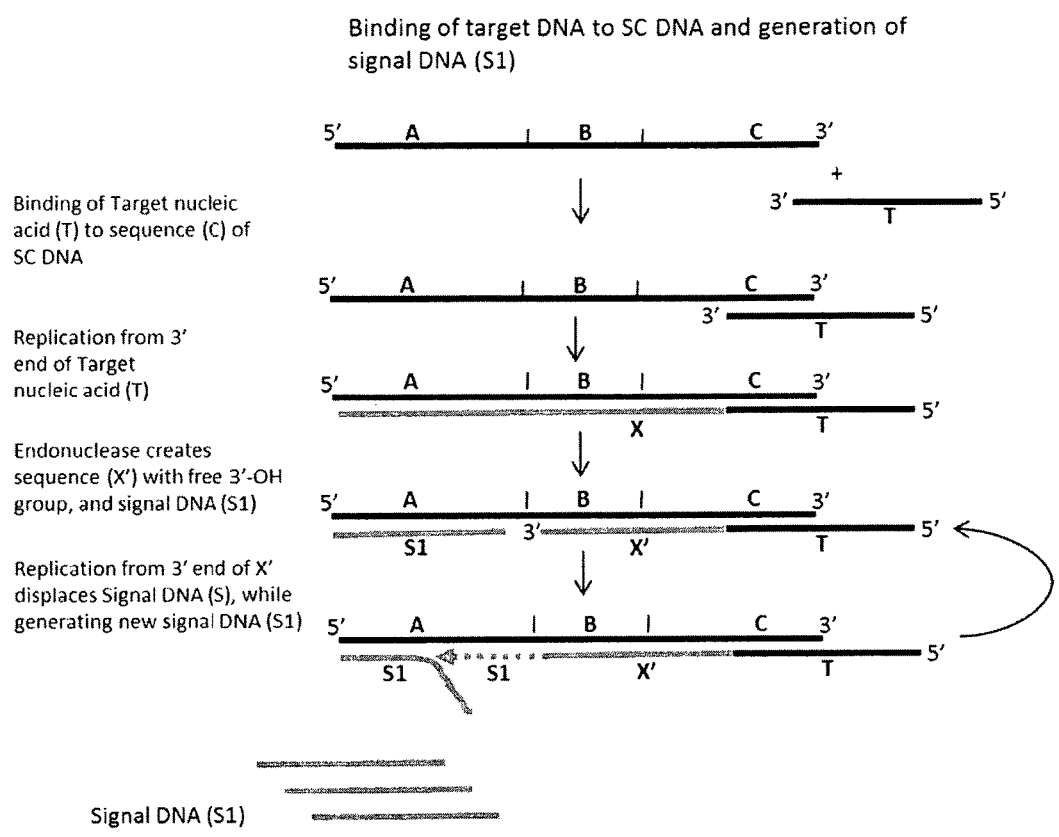
FIG. 2A is a diagram schematically illustrating the progression of an exemplary reaction of a target (T) nucleic acid with a Sequence Conversion (SC) DNA for the detection of a target nucleic acid in a sample. Sequences (A)-(C) are as described in FIG. 1A, sequence (T) represents a target sequence, sequence (X) represents the sequence produced when Target (T) bound to sequence (C) is extended by polymerase, sequence (X') represents the nicked extension sequence, and sequence (S1) represents the first signal DNA sequence eventually produced upon binding of the target (T) nucleic acid to the SC DNA.

As described in greater detail below, binding of a target nucleic acid to the complementary sequence (C) of the SC DNA primes replication via DNA polymerase to create an active, double-stranded form of the endonuclease recognition site (B) that can now serve as a recognition site for an endonuclease (FIG. 2A). Endonuclease nicking at the newly created double-stranded endonuclease site (B), or at a site adjacent to newly created double-stranded endonuclease site (B), then primes replication via DNA polymerase and generates a first signal DNA (S1) (see, e.g., FIG. 2A). As illustrated in FIG. 2A, the endonuclease recognition site (B) is oriented such that the newly replicated strand is nicked, not the SC DNA. That is, when the newly replicated strand is generated the orientation of the endonuclease recognition site in (B) directs endonuclease activity (cleavage) of the newly replicated strand. As such, the endonuclease recognition site comprises a sequence that is complementary to a sequence that is nicked by an endonuclease, allowing the SC oligonucleotide to remain intact throughout the reaction (i.e., the SC DNA is not nicked or cleaved).

Figure 2B:
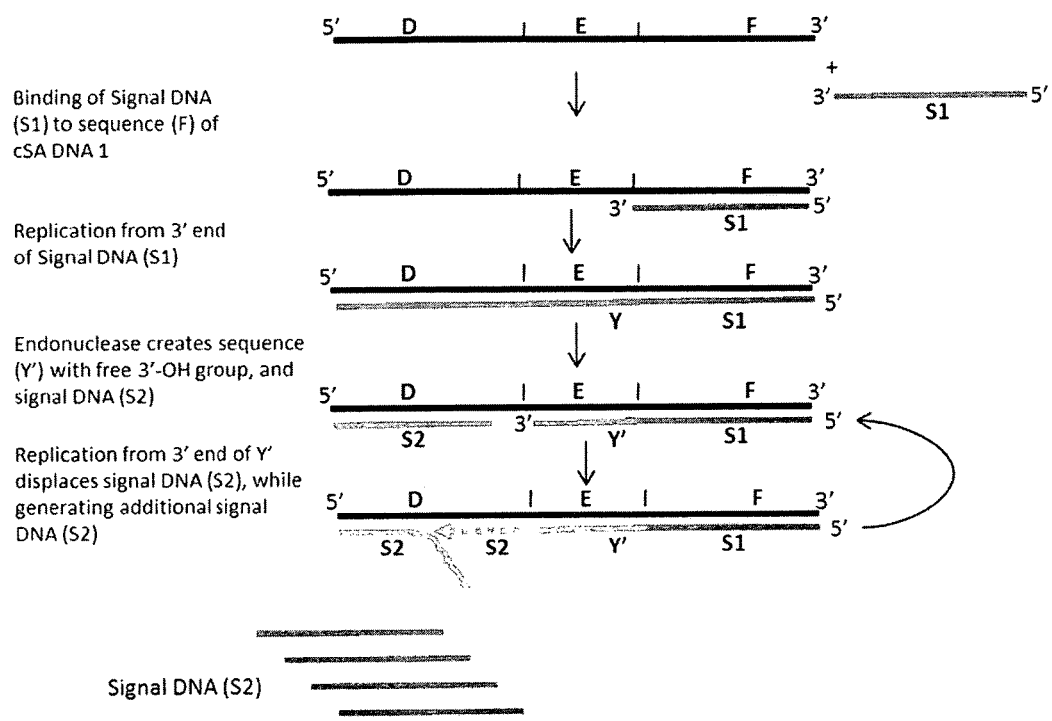
FIG. 2B is a diagram schematically illustrating the progression of an exemplary reaction of a signal DNA (S1) with a first cascade Signal Amplifier DNA 1 (cSA DNA 1) for the detection of a target nucleic acid in a sample. Sequences (D)-(F) are as described in FIG. 1B, sequence (S1) is the Signal DNA produced from reaction of Target (T) nucleic acid with SC DNA as described in FIG. 2A, sequence (Y) represents the sequence produced when Signal DNA (S1) bound to sequence (D) is extended by polymerase, sequence (Y') represents the nicked extension sequence, and sequence (S2) represents the unique signal DNA sequence eventually produced. Because the cSA DNA 1 signal generation sequence (D) is non-homologous to the SC signal generation sequence (A), a different unique signal DNA (S2) is produced.

As described in greater detail below, binding of a first signal DNA (S1), generated from the signal generation sequence (A) of a SC DNA, to the sequence (F) of a cSA DNA 1 primes replication via DNA polymerase to create an active, double-stranded form of the endonuclease recognition site (E) of the cSA DNA 1 that can serve as a recognition site for an endonuclease (FIG. 2B). Endonuclease nicking at the newly created double-stranded endonuclease site (E) of the cSA DNA 1, or at a site adjacent to newly created double-stranded endonuclease site (E), then primes replication via DNA polymerase and generates a second signal DNA (S2) that is different from the first signal DNA (S1) generated from the SC DNA (FIG. 2B). As illustrated in FIG. 2B, the endonuclease recognition site (E) is oriented such that the newly replicated strand is nicked, not the cSA DNA 1. That is, when the newly replicated strand is generated the orientation of the endonuclease recognition site in E directs endonuclease activity (cleavage) of the newly replicated strand. As such, the endonuclease recognition site comprises a sequence that is complementary to a sequence that is nicked by an endonuclease, allowing the cSA DNA 1 oligonucleotide to remain intact throughout the reaction (i.e., the cSA DNA 1 is not nicked or cleaved).

The sequence (C) of the SC DNA that is complementary to the target DNA is not limited by length, and can be from about 5 to about 100 nucleic acid bases, and all integers between 5 and 100. In some embodiments, the sequence (C) of the SC DNA is from about 5 to about 30 nucleic acid bases, and all integers between 5 and 30. In some embodiments, the sequence (C) in the SC DNA is from about 10 to about 30 nucleic acid bases, and all integers between 10 and 30. In further embodiments, the sequence (C) of the SC DNA is from about 15 to about 30 nucleic acid bases, and all integers between 15 and 30.

Complementary sequences are capable of forming hydrogen bonding interactions to form a double stranded nucleic acid structure (e.g., nucleic acid base pairs). For example, a sequence that is complementary to a first sequence includes a sequence which is capable of forming Watson-Crick base-pairs with the first sequence. As used herein, the term "complementary" does not require that a sequence is complementary over the full-length of its complementary strand, and encompasses a sequence that is complementary to a portion of another sequence. Thus, in some embodiments, a complementary sequence encompasses sequences that are complementary over the entire length of the sequence or over a portion thereof (e.g., greater than about 10%, about 20%, about 30%, about 40%, about 50%, about 60%, about 70%, about 80%, or about 90% of the length of the sequence). For example, two sequences can be complementary to each other over a length ranging from about 2 to about 100 consecutive (contiguous) nucleotides, or any integer between 2 and 100. In some embodiments, two sequences can be complementary to each other over a length ranging from about 15 to about 30 consecutive (contiguous) nucleotides, or any integer between 15 and 30. As used herein, complementary sequences can encompass sequences that have some sequence mismatches. For example, complementary sequences can include sequences that are complementary to at least about 70% to 100%, preferably greater than above 95% of the length of the sequence. Despite some amount of mismatches, complementary sequences generally have the ability to selectively hybridize to one another under appropriate conditions such as, for example, stringent and highly stringent conditions such as those described herein or generally known by those of ordinary skill in the art.

The SC and cSA DNAs may be synthesized by known methods. For example, the SC and cSA DNAs can be synthesized using a phosphoramidite method, a phosphotriester method, an H-phosphonate method, or a thiophosphonate method. In some embodiments, the SC and/or cSA DNAs can be purified, for example using ion exchange HPLC.

The SC and cSA DNAs may comprise chemical modifications such as are generally known in the art. In some embodiments, for example, the SC and cSA DNAs can comprise chemically modified nucleotides (e.g., 2'-0 methyl derivative, phosphorothioates, etc.), 3' end modifications, 5' end modifications, or any combinations thereof. In some embodiments, the 3' end of the SC and cSA DNAs may be modified such that an extension reaction does not occur from the 3' end of the SC or cSA DNA (e.g., upon binding of a target sequence, or another non-target sequence, that might serve as a primer for polymerase extension). As illustrated in FIG. 2A, it is the 3' end of the target nucleic acid (T), not the SC DNA, which initiates DNA replication. Any replication initiated from the 3' end of the SC or cSA DNAs may lead to detection errors (e.g., false positives). Further, non-specific extension reactions from an unmodified 3' end of the SC DNA arising from events such as, for example, binding between the SC DNA and a non-target sequence, binding between the SC DNA and a target sequence at an incorrect position, binding between SC and cSA DNAs, or non-templated de novo or ab initio DNA synthesis may also lead to detection errors. Accordingly, in embodiments, the SC and cSA DNAs comprise a 3' end modification that can reduce or eliminate the occurrence of any non-desired extension reactions, such as those discussed above. Non-limiting examples of 3'-end modifications include TAMRA, DABCYL, and FAM. Other non-limiting examples of modifications include, for example, biotinylation, fluorochromation, phosphorylation, thiolation, amination, inverted nucleotides, or abasic groups.

In another aspect, the present invention encompasses methods for detecting a target nucleic acid (T) in a sample. The methods generally comprise contacting said sample with: a first oligonucleotide (sequence conversion DNA or SC DNA) comprising, in the 5' to 3' direction, a first signal DNA generation sequence (A), an endonuclease recognition site (B), and a sequence (C) complementary to the 3' end of a target nucleic acid; a second oligonucleotide (cascade signal amplifier DNA 1 or cSA DNA 1) comprising, in the 5' to 3' direction, a second unique signal DNA generation sequence (D), an endonuclease recognition site (E), and a sequence (F) that is homologous to the first signal DNA generation sequence (A) of the first SC DNA oligonucleotide; and a third oligonucleotide (cascade signal amplifier DNA 2 or cSA DNA 2) comprising, in the 5' to 3' direction, a third unique signal DNA generation sequence (G), an endonuclease recognition site (H), and a sequence (I) that is homologous to the second signal DNA generation sequence (D) of the second oligonucleotide cSA DNA 1; a polymerase; and at least one endonuclease for a nicking reaction. In embodiments of this aspect, the method also comprises determining the presence or absence of a signal DNA, wherein the presence of the signal DNA indicates the presence of the target nucleic acid in the sample.

The method comprises contacting a sample with an endonuclease. The endonuclease may be a nicking endonuclease or a restriction endonuclease that is capable of or that can be used in nicking the sequence complementary to the endonuclease recognition site (B) within the SC DNA, the sequence complementary to the endonuclease recognition site (E) within the first cSA DNA 1, and the sequence complementary to the endonuclease recognition site (H) within the second cSA DNA 2. In some embodiments, the endonuclease comprises a nicking endonuclease or a restriction endonuclease that can catalyze or can be used to catalyze a double-stranded DNA nicking reaction. In embodiments providing a nicking endonuclease, the phosphodiester linkage of one strand of a double-strand DNA may be cleaved to generate a phosphate group on the 5' side of the cleavage site and a hydroxyl group on the 3' side. Non-limiting examples of nicking endonucleases include Nb.BbvCI, Nt.AlwI, Nt.BbvCI, Nb.BsrDI, Nb.BtsI, Nt.BspQI, Nt.BstNBI, Nb.BsmI, Nt.CviPII, and Nt.BsmAI.

In some embodiments, the endonuclease may be a restriction endonuclease. In these embodiments the restriction endonuclease recognition site may be modified so that the restriction endonuclease cleaves the phophodiester bond on only one strand of a double stranded DNA, and generates a nick in the double strand. Methods or strategies may be used to modify the activity of the restriction endonuclease such as, for example, including a chemical modification in at least one strand of a double-stranded nucleic acid that is not cleaved by the restriction enzyme. One non-limiting example of such a modification includes replacing the oxygen atom of phosphodiester linkage of one strand with a sulfur atom.

In embodiments providing a restriction endonuclease, the phosphodiester linkage of one strand of a double-strand DNA may be cleaved to generate a phosphate group on the 5' side of the cleavage site and a hydroxyl group on the 3' side. Non-limiting examples of restriction endonucleases include Hinc II, Hind II, Ava I, Fnu4HI, Tth111I and NciI.

The method comprises contacting a sample with a polymerase. In some embodiments, the polymerase may be a DNA polymerase having strand displacement activity. In some embodiments, the polymerase may be a polymerase that lacks 5'-3' exonuclease activity, lacks 3'-5' exonuclease activity, or lacks both 5'-3' and 3'-5' exonuclease activity. The polymerase may be eukaryotic, prokaryotic, or viral in origin, and can also be genetically modified. In some embodiments, the polymerase is selected from among those that function at lower temperatures, including ambient (e.g., room) temperatures. Non-limiting examples of DNA polymerases include Klenow fragments, DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus caldotenax*.

Figure 2C:
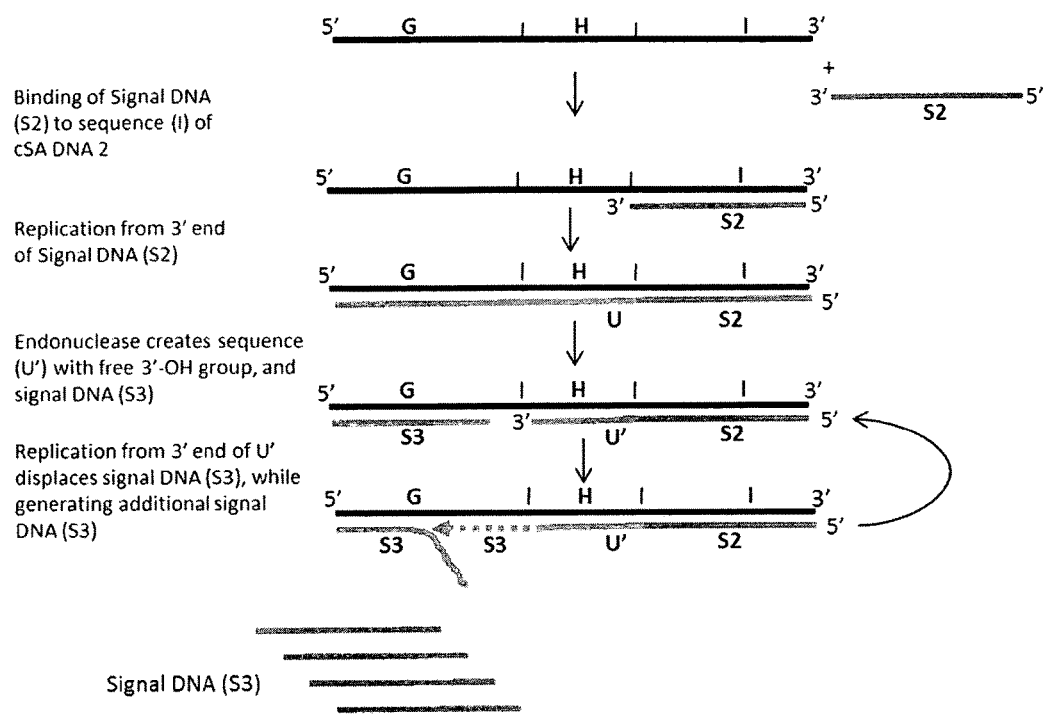
FIG. 2C is a diagram schematically illustrating the progression of an exemplary reaction of a signal DNA (S2) with a second cascade Signal Amplifier DNA 2 (cSA DNA 2) for the detection of a target nucleic acid in a sample. Sequences (G)-(I) are as described in FIG. 1C, signal sequence (S2) is the Signal DNA produced as described in FIG. 2B, sequence (U) represents the sequence produced when Signal DNA (S2) bound to sequence (I) is extended by polymerase, sequence (U') represents the nicked extension sequence, and sequence (S3) represents the unique signal DNA sequence eventually produced. Because the cSA DNA 2 signal generation sequence (G) is non-homologous to the cSA signal generation sequence (D), a different unique signal DNA (S3) is produced.

One non-limiting embodiment of the methods disclosed herein is illustrated in FIGS. 2A, 2B, and 2C. Briefly, as illustrated in FIG. 2A, a sample is contacted with SC DNA in the presence of a DNA polymerase and an endonuclease capable of nicking the double-stranded form (i.e., complementary sequence) of the endonuclease recognition site (B), or a site adjacent to the double-stranded form of the endonuclease recognition site (B). If a target nucleic acid (T) is present in the sample, the 3' end sequence of the target nucleic acid (T) hybridizes to the sequence (C) of the SC DNA which is complementary to the target and primes or initiates replication (by the DNA polymerase present in the reaction mixture) thereby generating double stranded extension sequence (X) that includes the double stranded endonuclease recognition site (B). Recognition of the newly-generated double stranded endonuclease recognition site (B) (by the endonuclease present in the reaction mixture), and subsequent nicking of the newly-generated strand (by the endonuclease present in the reaction mixture), generates a first oligonucleotide signal DNA 1 (S1) and extension sequence (X'). Because the 3'-OH of sequence (X') at the nick serves as an initiation site for subsequent rounds of strand displacement replication, oligonucleotide (S1) is displaced from the SC DNA by DNA polymerase which continues to replicate and amplify signal DNA 1 (S1) in the reaction mixture.

As further illustrated in FIG. 2B, the first signal DNA (S1) produced by interaction of a Target (T) nucleic acid with a SC DNA can be converted to a second signal DNA 2 (S2) by the presence of a first cascade signal amplifier DNA 1 (or cSA DNA 1). Briefly, a first signal DNA 1 (S1) present in a reaction hybridizes to the sequence (F) of the first cSA DNA 1 which primes or initiates replication (by the DNA polymerase present in the reaction mixture) thereby generating double stranded extension sequence (Y) that includes the double stranded endonuclease recognition site (E). Recognition of the newly-generated double stranded endonuclease recognition site (E) (by endonuclease present in the reaction mixture), and subsequent nicking of the newly-generated strand (by endonuclease present in the reaction mixture), generates a different oligonucleotide signal sequence (S2) and extension sequence (Y'). Because the 3'-OH of sequence (Y') at the nick serves as an initiation site for subsequent rounds of strand displacement replication, oligonucleotide (S2) is displaced from the cSA DNA 1 by DNA polymerase which continues to replicate and amplify a second unique signal DNA 2 (S2) in the reaction mixture.

As further illustrated in FIG. 2C, the second signal DNA (S2) produced by interaction of the first signal DNA (S1) with a first cascade SA DNA (cSA DNA 1) can be converted to a third signal DNA 3 (S3) by the presence of a second cascade signal amplifier DNA 2 (or cSA DNA 2). Briefly, a second signal DNA 2 (S2) present in a reaction hybridizes to the sequence (I) of the second cSA DNA 2 which primes or initiates replication (by the DNA polymerase present in the reaction mixture) thereby generating double stranded extension sequence (U) that includes the double stranded endonuclease recognition site (H). Recognition of the newly-generated double stranded endonuclease recognition site (H) (by endonuclease present in the reaction mixture), and subsequent nicking of the newly-generated strand (by endonuclease present in the reaction mixture), generates a different oligonucleotide signal sequence (S3) and extension sequence (U'). Because the 3'-OH of sequence (U') at the nick serves as an initiation site for subsequent rounds of strand displacement replication, oligonucleotide (S3) is displaced from the cSA DNA 2 by DNA polymerase which continues to replicate and amplify a third unique signal DNA 3 (S3) in the reaction mixture.

In some embodiments, the Signal DNA (S2)/Target DNA ratio is from about 100 to about 1000, from about 100 to about 800, from about 100 to about 600, from about 100 to about 400, or from about 100 to about 200. In other embodiments, the Signal DNA (S3)/Target DNA ratio is from about 1000 to about 10000, from about 1000 to about 8000, from about 1000 to about 6000, from about 1000 to about 4000, or from about 1000 to about 2000.

Methods according to the invention may be performed under isothermal or substantially constant temperature conditions. In embodiments that relate to performing the method under a substantially constant temperature, some fluctuation in temperature is permitted. For example, in some embodiments a substantially constant temperature may fluctuate within a desired or identified target temperature range (e.g., about +/−2° C. or about +/−5° C.). In embodiments, a substantially constant temperature may include temperatures that do not include thermal cycling. In some embodiments, methods can be performed at isothermal or substantially constant temperatures such as, for example, (1) temperatures at or below about the calculated/predicted or experimentally determined optimal hybridization or annealing temperature of the target nucleic acid (T) to sequence (C) of the SC DNA; (2) temperatures at or below the melting temperature of the target nucleic acid (T) bound to SC DNA (typically, hybridization or annealing temperatures are slightly below the melting temperature); (3) temperatures at or below the melting temperature of a signal DNA (S) bound to a cSA DNA; or (4) temperatures at or about the calculated/predicted or experimentally determined optimal reaction temperature for the polymerase and/or endonuclease present in the reaction mixture.

The methods may comprise reaction temperatures that range from about 20° C. to about 70° C., including lower temperatures falling within the range of about 20° C. to about 42° C. In some embodiments, the reaction temperature range is from 35° C. to 40° C. (e.g., 35° C., 36° C., 37° C., 38° C., 39° C., or 40° C.). In other embodiments, the reaction temperature is below 65° C., including lower temperatures below about 55° C., about 50° C., about 45° C., about 40° C., or about 30° C. In still other embodiments, reaction temperatures may be about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C.

The methods may be performed for a time that is adequate to allow for amplification of a detectable amount of signal sequence in the presence of a target nucleic acid. In some embodiments, the reaction time may range from about 5 minutes to 16 hours, or from about 3 minutes to 16 hours. In still other embodiments, the reaction time may range from about 5 to 120 minutes, or from about 15 to 60 minutes.

Because the various signal DNAs (S1), (S2), and (S3) are generated only in the presence of the target nucleic acid (T), methods according to the present invention detect the presence or absence of a target nucleic acid (T) in a sample by detecting the presence or absence of any one signal DNA. The signal DNAs (S1), (S2), and (S3) are different, and are not limited by sequence, and can be any sequence that is amenable to detection. The signal DNAs (S1), (S2), and (S3) are also not limited by length. Preferably, the signal DNAs (S1), (S2), and (S3) can be from about 5 to about 100 bases, and any integer between 5 and 100. In some embodiments, the signal DNAs (S1), (S2), and (S3) can be from about 5 to about 30 nucleic acid bases, and all integers between 5 and 30. In some embodiments, the signal DNAs (S1), (S2), and (S3) can be from about 10 to about 30 bases in length and all integers between 10 and 30. In yet further embodiments, the signal DNAs (S1), (S2), and (S3) can be from about 15 to about 30 bases in length and all integers between 15 and 30.

Methods according to the disclosure may be performed under buffer conditions that comprise a pH range from about 4 to about 10, or from about 7 to about 9. The buffer may comprise a salt concentration from about 10 mM to about 500 mM, or from about 50 mM to 150 mM. In some embodiments the method may be performed using an amount of SC and/or cSA DNAs that allows for amplification of a detectable amount of signal sequence in the presence of a target nucleic acid. In some embodiments, the SC and/or cSA DNA concentration may range from about 100 pM to about 100 µM, from about 1 nM to about 150 nM, from about 5 nM to about 50 nM, or from about 5 nM to about 25 nM.

The presence of any one signal DNA (S1), (S2), and/or (S3) can be detected by any method known in the art. For example, gel electrophoresis and staining with ethidium bromide can be used. Also, the presence of any one signal DNA (S1), (S2), and/or (S3) can be detected using fluorescence polarization, immunoassay, fluorescence resonance energy transfer, enzyme labeling (such as peroxidase or alkaline phosphatase), fluorescent labeling (such as fluorescein or rhodamine), chemiluminescence, bioluminescence, surface plasmon resonance (SPR), or a fluorophore-modified probe DNA (e.g., TaqMan probe). The amplification product can also be detected by using a labeled nucleotide labeled with a biotin, for example. In such a case, the biotin in the amplification product can be detected using fluorescence-labeled avidin or enzyme-labeled avidin, for example. The amplification product can also be detected with electrodes by using redox intercalator known to those skilled in the art. The amplification product can also be detected using surface plasmon resonance (SPR), a Quarts Crystal Microbalance (QCM), or electrochemical methods (including those methods employing nanopore sensors).

The methods according to the present invention detect the presence or absence of a target nucleic acid (T) in a sample. The methods according to the present invention can also be used to quantitatively measure the concentration of a target nucleic acid in a test sample. For example, methods according to the present disclosure can be performed in the presence of a range of different known concentrations of the target nucleic acid, and calibration curves can be prepared and used as generally practiced in the art.

The target nucleic acid (T) in FIG. 2A) can comprise any nucleic acid sequence and can include DNA, RNA, chemically modified nucleic acids, non-natural nucleic acids, nucleic acid analogs, or any hybrid or combination thereof. Accordingly, in some embodiments, DNA may include cDNA, genomic DNA, and synthetic DNA, and RNA may include total RNA, mRNA, rRNA, siRNA, hnRNA, piRNA, aRNA, miRNA, and synthetic RNA. While some embodiments relate to particular target nucleic acid sequences, any nucleic acid sequence, including auxiliary nucleic acid sequence, can be a target nucleic acid sequence to be detected. The disclosure provides for the detection of a target nucleic acid with selectivity and sensitivity even when the nucleic acid is a short-chain nucleic acid. Accordingly, the degree of complementarity between sequences (C) of the SC DNA and target nucleic acid (T) allows for specific hybridization between the sequences (e.g., the number of complementary nucleotides in sequence (C) of the sequence conversion DNA and target nucleic acid (T) sequences avoids non-specific hybridization under a given set of reaction conditions).

In embodiments, the target nucleic acid sequence can be from, or derived from any number of sources including, for example, genomic DNA, expressed mRNA, nucleic acid sequences from pathogens (microbes, viruses), or therapeutic nucleic acids. Accordingly, the SC and cSA DNAs and the methods disclosed herein may be used for the diagnosis and prognosis of diseases (e.g., arising from genetic and infectious sources), identification of contaminants (e.g., food-borne illnesses, equipment contamination), personalized medicine (e.g., monitoring and/or prognosis of a therapy), and the like. For example, molecular diagnostic testing can be performed with respect to the following infectious diseases: Hepatitis B Virus (HBV); hepatitis C (HCV); HCV (genotypes 1-6); Human Immunodeficiency Virus type 1 (HIV-1); Chlamydia trachomatis; Neisseria gonorrhoeae; influenza A; influenza B; Respiratory Syncytial Virus (RSV); and Parvo virus.

In some embodiments, the target nucleic acid can comprise microRNAs (miRNA). microRNAs include small non-coding RNA molecules of about 22 nucleotides. microRNAs are known to function in transcription and post-transcriptional regulation of gene expression. It is known that micro-RNAs function by base pairing with complementary regions of messenger RNA (mRNA), resulting in gene silencing via translational repression or target degradation.

Any type of sample that may comprise a target nucleic acid may be used in the methods disclosed herein. As such, the sample containing or suspected of containing a target nucleic acid is not specifically limited, and includes, for example, biological samples derived from living subjects, such as whole blood, serum, buffy coat, urine, feces, cerebrospinal fluid, seminal fluid, saliva, tissue (such as cancerous tissue or lymph nodes), cell cultures (such as mammalian cell cultures or bacterial cultures); samples containing nucleic acids, such as viroids, viruses, bacteria, fungi, yeast, plants, and animals; samples (such as food and biological preparations) that may contain or be infected with microorganisms such as viruses or bacteria; and samples that may contain biological substances, such as soil, industrial process and manufacturing equipment, and wastewater; and samples derived from various water sources (e.g., drinking water). Furthermore, a sample may be processed by any known method to prepare a nucleic acid-containing composition used in the methods disclosed herein. Examples of such preparations can include cell breakage (e.g., cell lysates and extracts), sample fractionation, nucleic acids in the samples, and specific nucleic acid molecular groups such as mRNA-enriched samples. The sample used in the method for detecting a target nucleic acid of the present invention is not limited to those derived from biological and natural products as mentioned above and may be a sample containing a synthetic oligonucleotide.

Methods according to the present invention can be performed in combination with the Abbott m2000sp sample preparation system. The m2000sp uses magnetic particle technology to capture nucleic acids and washes the particles to remove unbound sample components. The bound nucleic acids are eluted and transferred to a 96 deep-well plate. The Abbott m2000sp can also combine with the washed nucleic acids transferred to the 96 deep-well plate any reagents required to perform the methods according to the present technology. For example, SC and cSA DNAs, polymerases, endonucleases, molecular beacons, and any other reagent (e.g., dNTPs) can be added as required, or desired.

Methods according to the present invention can also be interfaced with point-of-care platforms. For example, the incorporation of a deoxyribonucleotide triphosphate (dNTP) into a growing DNA strand involves the formation of a covalent bond and the release of pyrophosphate and a positively charged hydrogen ion affecting the pH of a reaction. As such, the synthesis of signal DNA according to methods of the present invention can be detected by tracking changes in pH using, for example, point-of-care micro-pH meters. For example, Abbott's i-STAT point-of-care system can be supplied with single-use disposable cartridges containing micro fabricated sensors, calibration solutions, fluidic systems, and waste chambers for analysis of pH.

The methods disclosed herein can comprise additional reagents. Some non-limiting examples of other reagents that can be used in the nucleic acid amplification reaction include metallic salts such as sodium chloride, magnesium chloride, magnesium acetate, and magnesium sulfate; substrates such as dNTP mix; and buffer solutions such as Tris-HCl buffer, tricine buffer, sodium phosphate buffer, and potassium phosphate buffer. Likewise, detergents, oxidants and reducing agents can also be used in the practice of the methods disclosed herein. Furthermore, agents such as dimethyl sulfoxide and betaine (N,N,N-trimethylglycine); acidic substances described in International Publication No. WO 99/54455; and cationic complexes can be used.

The methods and nucleic acid structures provided herein may be used in combination with other methods to provide for the exponential amplification of a signal DNA in the presence of a target nucleic acid. For example, the methods and compositions according to the present disclosure may be used in combination with covered sequence conversion DNAs, as described in U.S. Provisional Application 61/927, 710, entitled "Covered Sequence Conversion DNA and Detection Methods" which is incorporated herein by reference. The methods and compositions according to the present disclosure may also be used in combination with chemically modified sequence conversion and signal amplifier DNAs, as described in U.S. Provisional Application 62/063, 666, entitled "Sequence Conversion and Signal Amplifier DNA Having Locked Nucleic Acids and Detection Methods Using Same" which is incorporated herein by reference.

The term "about" generally refers to a range of numbers that one of skill in the art would consider equivalent to the recited value (i.e., having the same function or result). The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The Examples that follow are intended to be illustrative of the aspects and embodiments described above. Neither the above disclosure nor the Examples below should be viewed as limiting to the scope of the appended claims. One of skill in the art will appreciate that the disclosure is not limited by the particular terminology which is used to describe and illustrate the various aspects of the disclosure.

EXAMPLE 1

A two-step cascade signal DNA amplification reaction was performed to detect a target nucleic acid in a sample. The two-step reaction was performed using a SC DNA having the sequence 5'-TGATAGCCCTGTACAATGC-CTCAGCTTGTACAGGGCTATCACTGTTCCTGCT-GAA-idT-idT-3' (SEQ ID NO.:1;) in combination with cSA DNA 2 having the sequence 5'-ACTGCCCTAAGTGCTC-CTCCTCAGCAGGAGCACTTAGGGCAGTTGATAGC-CCTGTACAATG-idT-idT-3' (SEQ ID NO.:2;). u.particles DNA (SEQ ID NO.: 3) and conjugate DNA (SEQ ID NO.: 4) were used to detect the production of a second signal DNA (S2) from the cSA DNA 1 (SEQ ID NO.:6;).

The reactions were performed at 37° C. in a 120 µL reaction volume containing New England Biolabs (NEB)

Buffer 2 having a final concentration of 10 mM Tris-HCl, 50 mM NaCl, 10 mM MgCl2, 1 mM DTT, 0.1% Tween 20, pH 7.9. The nicking endonuclease used in each reaction was Nb.BbvCI, which was present at a concentration of 0.1 units/μL. The polymerase used in each reaction was Bst DNA Polymerase Large Fragment, which was present at a concentration of 0.08 units/μL. The dNTPs were present at a final concentration 100 μM each. SC and cSA DNA 1 were present in the reaction at a final concentration of 1.4 nM and 4.2 nM, respectively. Chemiluminescent measurements were performed using ARCHITECT.

The target nucleic acid, which was the same DNA sequence as human hsa-miR-24 (SEQ ID NO.: 5), was present at concentrations of 0.5 pM, 1 pM, 5 pM, and 10 pM. As shown in Table 1, the Signal DNA (S2)/Target DNA ratio was from about 240 to about 300.

TABLE 1

| [Target DNA] pM | [Signal DNA 2] pM | [Signal DNA 2]/ [Target DNA] |
| --- | --- | --- |
| 0.5 | 132 | 264 |
| 1.0 | 245 | 245 |
| 5.0 | 1329 | 266 |
| 10 | 2912 | 291 |

EXAMPLE 2

A three-step cascade signal DNA amplification reaction was performed to detect a target nucleic acid in a sample. The three-step cascade method included contacting a sample having a target nucleic acid with: a sequence conversion DNA (SC DNA) comprising, in the 5' to 3' direction, a first signal DNA generation sequence, an endonuclease recognition site, and a sequence complementary to the 3' end of a target nucleic acid; a first cascade signal amplifier DNA 1 (cSA DNA 1) comprising, in the 5' to 3' direction, a second unique signal DNA generation sequence, an endonuclease recognition site, and a sequence that was homologous to the first signal DNA generation sequence of the SC DNA oligonucleotide; a second cascade signal amplifier DNA 2 (cSA DNA 2) comprising, in the 5' to 3' direction, a third unique signal DNA generation sequence, an endonuclease recognition site, and a sequence that was homologous to the second signal DNA generation sequence of the first cSA DNA 1; a polymerase; and an endonuclease for a nicking reaction.

The three-step reaction was performed using a SC DNA having the sequence 5'-GCGATGATGATCCTCAGCG-GATCATCATCGCCTGTTCCTGCTGAACTGAGCCA idT-3' (SEQ ID NO.:7;) in combination with a first cSA DNA 1, having the sequence 5'-TGATAGCCCTGTACAAT-GCCTCAGCTTGTACAGGGCTATCAGCGATGAT-GATCCTCA-idT-3' (SEQ ID NO.:8;), and a second cSA DNA 2, having the sequence 5'-ACTGCCCTAAGTGCTC-CTCCTCAGCAGGAGCACTTAGGGCAGTTGATAGC-CCTGTACAATG-idT-idT-3' (SEQ ID NO.:2;). u.particles DNA (SEQ ID NO.: 3) and conjugate DNA (SEQ ID NO.: 4) were used to detect the production of a third signal DNA (S3) from cSA DNA 2 (SEQ ID NO.:6).

The reactions were performed at 37° C. in a 120 μL reaction volume containing New England Biolabs (NEB) Buffer 2 having a final concentration of 10 mM Tris-HCl, 50 mM NaCl, 10 mM MgCl2, 1 mM DTT, 0.1% Tween 20, pH 7.9. The nicking endonuclease used in each reaction was Nb.BbvCI, which was present at a concentration of 0.1 units/μL. The polymerase used in each reaction was Bst DNA Polymerase Large Fragment, which was present at a concentration of 0.08 units/μL. The dNTPs were present at a final concentration 200 μM each. SC, cSA DNA 1, and cSA DNA 2 were present in the reaction at a final concentration of 1.4 nM, 4.2 nM, and 4.2 nM respectively. Chemiluminescent measurements were performed using ARCHITECT.

The target nucleic acid, which was the same DNA sequence as human hsa-miR-24 (SEQ ID NO.: 5), was present at concentrations of 0.025 pM, 0.05 pM, 0.1 pM, 0.2 pM, 0.5 pM, and 1 pM. As shown in Table 2, the Signal DNA (S3)/Target DNA ratio was from about 4,500 to about 7,000.

TABLE 2

| [Target DNA] pM | [Signal DNA 3] pM | [Signal DNA 3]/ [Target DNA] |
| --- | --- | --- |
| 0.025 | 119 | 4751 |
| 0.05 | 264 | 5287 |
| 0.1 | 597 | 5973 |
| 0.2 | 1132 | 5659 |
| 0.5 | 3217 | 6434 |
| 1.0 | 6735 | 6735 |

EXAMPLE 3

As discussed herein, certain aspects and embodiments of the disclosure provide a loop amplification method for detecting a target nucleic acid in a sample. In some embodiments, the target nucleic acid interacts with a first oligonucleotide (sequence conversion DNA or SC DNA) to produce a first Signal DNA (S1) that in turn interacts with a second oligonucleotide (cascade signal amplifier DNA 1 or cSA DNA 1) to produce a second signal DNA (S2) different from S1, which in turn interacts with a third oligonucleotide (cascade signal amplifier DNA 2 or cSA DNA 2) to produce Signal DNA (S1), which is the same Signal DNA (S1) generated upon interaction of the target nucleic acid with the first oligonucleotide or SC DNA. In this embodiment, amplified Signal DNA (S2) is converted to Signal DNA (S1) upon interaction with a cascade signal amplifier DNA cSA DNA 2, allowing cyclic amplification of signal DNA (S1).

Figure 3:
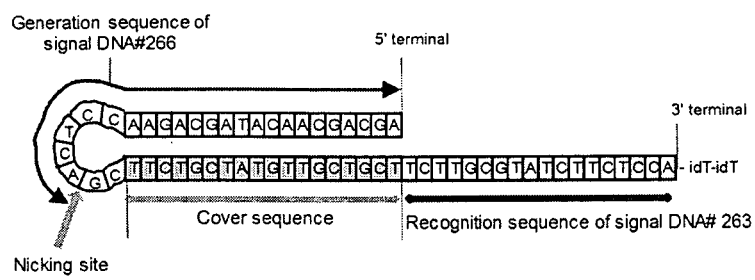
FIG. 3 depicts converter DNA #265 (SEQ ID NO.: 11) and converter DNA #429 in FIG. 3 (SEQ ID NO.: 12).
Figure 3:
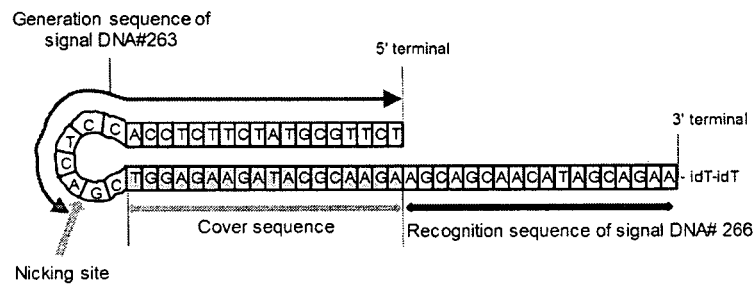

To provide an illustrative example of the loop amplification method described above, a polymerase, a nicking endonuclease, and a Signal DNA S1 to be amplified (signal DNA #263 in FIG. 3; SEQ ID NO.: 9 having the sequence 5'-TGGAGAAGATACGCAAGA-3') was mixed, in the presence of reaction buffer and dNTPs, with 0.28 nM of a first cSA DNA 1 (converter DNA #265 in FIG. 3; (SEQ ID NO.: 11) and 0.28 nM of a second cSA DNA 2 (converter DNA #429 in FIG. 3; (SEQ ID NO.: 12). Reactions were analyzed using chemiluminescent detection and Abbott's ARCHITECT system.

As shown in FIG. 3, the first cSA DNA 1 (converter DNA #265 in FIG. 3; SEQ ID NO.: 11) has a recognition sequence for Signal DNA S1 (SEQ ID NO.: 9), the binding of which primes replication and results in the production of Signal DNA S2 (SEQ ID NO.: 10 having the sequence 5'-TTCT-GCTATGTTGCTGCT-3'). The second cSA DNA 2 (converter DNA #429 in FIG. 3; SEQ ID NO.: 12) has a recognition sequence for Signal DNA S2 (SEQ ID NO.: 10), the binding of which primes replication and the subsequent production of Signal DNA 1 (SEQ ID NO.: 9).

As illustrated in FIG. 3, both cSA DNA 1 (converter DNA #265 in FIG. 3; SEQ ID NO.: 11) and cSA DNA 2 (converter DNA #429 in FIG. 3; SEQ ID NO.: 12) had cover sequences complementary to their respective signal generation sequences (see generally, e.g., WO 2015/114469 or US PGPUB 2015/197823, entitled "Covered Sequence Conversion DNA and Detection Methods," incorporated herein by reference). The amplification ratio was about 419. The S/N of target (0.01 pM/0 pM) was about 2.0.

While the application has been described with reference to certain aspects and embodiments, it will be understood by those skilled in the art that changes may be made to the disclosure provided herein, and equivalents may be substituted without departing from the scope of the disclosure. Accordingly, the application should not be limited to the particular aspects and embodiments disclosed, but should be understood and appreciated to include all aspect and embodiments falling within the scope of the appended claims.

The invention claimed is:

1. A method for detecting a target nucleic acid in a sample, said method comprising contacting said sample with: a sequence oligonucleotide comprising, in the 5' to 3' direction, a first signal DNA generation sequence, an endonuclease recognition site, and a sequence complementary to the 3' end of said target nucleic acid, n unique cascade sequence amplification DNAs, wherein one of the n unique cascade sequence amplification DNAs comprises, in the 5' to 3' direction, a second signal DNA generation sequence that is different from the first signal DNA generation sequence of the sequence conversion DNA, an endonuclease recognition site, and a sequence that is homologous to the first signal DNA generation sequence of the sequence conversion DNA, wherein n is an integer between 1 and 10, a polymerase, and an endonuclease for a nicking reaction, to form a reaction mixture;

maintaining the reaction mixture under conditions that allow binding of the target nucleic acid to the sequence conversion DNA to prime replication and generate a first signal DNA; and detecting the presence or absence of at least one signal DNA generated by the signal generation sequence of the n unique cascade sequence amplification DNAs.

2. The method of claim 1, said method comprising two unique cascade sequence amplification DNAs wherein the second of the two unique cascade sequence amplification DNAs comprises, in the 5' to 3' direction, a third signal DNA generation sequence, an endonuclease recognition site, and a sequence that is homologous to the second signal DNA generation sequence of the first of the n unique cascade sequence amplification DNAs.

3. The method of claim 1, wherein said method is performed at a substantially constant temperature.

4. The method of claim 1, wherein said method is performed at a temperature of from about 20° C. to about 42° C.

5. The method of claim 1, wherein said polymerase has strand displacement activity.

6. The method of claim 1, wherein said polymerase is 3' to 5' exonuclease deficient, 5' to 3' exonuclease deficient, or both.

7. The method of claim 1 wherein said polymerase comprises a DNA polymerase selected from the group consisting of Klenow fragments of DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus caldotenax*.

8. The method of claim 1 wherein said endonuclease is an enzyme selected from the group consisting of Nb.BbvCI, Nt.AlwI, Nt.BbvCI, and Nt.BsmAI.

9. The method of claim 1 wherein said target is a microRNA.

10. The method of claim 1 wherein said target nucleic acid originates from an infectious agent.

* * * * *

UNITED STATES PATENT AND TRADEMARK OFFICE
CERTIFICATE OF CORRECTION

PATENT NO. : 10,604,790 B2
APPLICATION NO. : 14/998162
DATED : March 31, 2020
INVENTOR(S) : Makoto Komori and Toru Yoshimura It is certified that error appears in the above-identified patent and that said Letters Patent is hereby corrected as shown below:

In the Claims

Column 23, Lines 33-58 should read:
1. A method for detecting a target nucleic acid in a sample, said method comprising contacting said sample with: a sequence conversion DNA oligonucleotide comprising, in the 5' to 3' direction, a first signal DNA generation sequence, an endonuclease recognition site, and a sequence complementary to the 3' end of said target nucleic acid,
    n unique cascade sequence amplification DNAs, wherein
        one of the n unique cascade sequence amplification DNAs comprises, in the 5' to 3' direction, a second signal DNA generation sequence that is different from the first signal DNA generation sequence of the sequence conversion DNA, an endonuclease recognition site, and a sequence that is homologous to the first signal DNA generation sequence of the sequence conversion DNA,
        wherein n is an integer between 1 and 10,
    a polymerase, and
    an endonuclease for a nicking reaction,
to form a reaction mixture;
maintaining the reaction mixture under conditions that allow binding of the target nucleic acid to the sequence conversion DNA to prime replication and generate a first signal DNA; and
detecting the presence or absence of at least one signal DNA generated by the signal generation sequence of the n unique cascade sequence amplification DNAs.

Column 24, Lines 56-57 should read:
9. The method of claim 1 wherein said target nucleic acid is a micro-RNA.

Signed and Sealed this
Twenty-eighth Day of May, 2024

*Katherine Kelly Vidal*
Katherine Kelly Vidal
*Director of the United States Patent and Trademark Office*